United States Patent
Uemoto et al.

(10) Patent No.: US 9,024,280 B2
(45) Date of Patent: May 5, 2015

(54) COMPOSITE CHARGED PARTICLE BEAM APPARATUS

(71) Applicants: Atsushi Uemoto, Chiba (JP); Yo Yamamoto, Chiba (JP); Tatsuya Asahata, Chiba (JP)

(72) Inventors: Atsushi Uemoto, Chiba (JP); Yo Yamamoto, Chiba (JP); Tatsuya Asahata, Chiba (JP)

(73) Assignee: Hitachi High-Tech Science Corporation (JP)

( * ) Notice: Subject to any disclaimer, the term of this patent is extended or adjusted under 35 U.S.C. 154(b) by 0 days.

(21) Appl. No.: 13/622,028

(22) Filed: Sep. 18, 2012

(65) Prior Publication Data

US 2013/0075606 A1  Mar. 28, 2013

(30) Foreign Application Priority Data

Sep. 20, 2011 (JP) ................. 2011-204507

(51) Int. Cl.
*H01J 37/00* (2006.01)
*H01J 37/26* (2006.01)
*G01N 23/22* (2006.01)
*G01N 23/225* (2006.01)
*G01N 1/32* (2006.01)
*H01J 37/28* (2006.01)
*H01J 37/317* (2006.01)

(52) U.S. Cl.
CPC .......... *H01J 37/261* (2013.01); *G01N 23/2208* (2013.01); *G01N 23/225* (2013.01); *G01N 1/32* (2013.01); *G01N 2223/0816* (2013.01); *G01N 2223/102* (2013.01); *G01N 2223/105* (2013.01); *H01J 37/28* (2013.01); *H01J 37/317* (2013.01); *H01J 2237/20285* (2013.01); *H01J 2237/31745* (2013.01); *H01J 2237/31749* (2013.01)

(58) Field of Classification Search
CPC ............................. G01N 21/00; G01R 31/311
USPC ...................................... 250/492.1
See application file for complete search history.

(56) References Cited

U.S. PATENT DOCUMENTS

| | | | | |
|---|---|---|---|---|
| 5,760,892 | A * | 6/1998 | Koyama | 356/237.1 |
| 6,664,552 | B2 * | 12/2003 | Shichi et al. | 250/492.21 |
| 8,440,969 | B2 * | 5/2013 | Moore et al. | 250/307 |
| 2008/0265158 | A1 * | 10/2008 | Iwasaki | 250/310 |

FOREIGN PATENT DOCUMENTS

JP  06231720  8/1994

* cited by examiner

*Primary Examiner* — Phillip A Johnston
(74) *Attorney, Agent, or Firm* — Adams & Wilks

(57) ABSTRACT

A composite charged particle beam apparatus comprises an FIB column and an SEM column arranged so that the ion and the electron beam irradition axes intersect with each other substantially at a right angle. A sample stage mounts a sample, and a detector detects secondary particles generated from the sample when irradiated with the ion beam or the electron beam. An observation image formation portion forms an FIB image and an SEM image based on a detection signal of the detector. An optical microscope observes the sample, and a display portion displays the FIB image, the SEM image and an optical microscope image. A stage control portion changes the coordinate system of the sample stage to any selected one of the coordinate systems of the FIB image, the SEM image and the optical microscope image.

6 Claims, 6 Drawing Sheets

COMPOSITE CHARGED PARTICLE BEAM APPARATUS

BACKGROUND OF THE INVENTION

1. Field of the Invention

The present invention relates to a composite charged particle beam apparatus for observing a sample subjected to processing by a focused ion beam through a charged particle microscope.

2. Description of the Related Art

A focused ion beam apparatus is used for observation of a processed cross-section of a sample, production of a sample for transmission electron microscope observation, and other such purposes. Particularly in a composite charged particle beam apparatus including an electron beam apparatus, a cross-section which is under processing by a focused ion beam or a cross-section which has been processed by the focused ion beam can be observed in-situ by an electron beam. Such a composite charged particle beam apparatus is therefore widely used for successive cross-section observation and successive sample production.

In a general composite charged particle beam apparatus, the focused ion beam and the electron beam are arranged so that incident directions thereof form 90° or less, and hence the processed cross-section is observed by the electron beam from an oblique direction. In recent years, a three-dimensional analysis technology has been used in the wide field, in which images acquired for cross-section processing and its successive cross-section observation with the use of a composite charged particle beam apparatus are reconstructed into a three-dimensional image.

In the conventional composite charged particle beam apparatus, however, the processed cross-section is observed from a direction of 90° or less, and hence it is necessary to correct an observation image obtained in the oblique direction into a planar image. Further, as an observation site becomes finer, there is an increasing need for observation of a sample under processing through a scanning transmission electron microscope.

As one solution to meet the need, a technology using a composite charged particle beam apparatus in which an electron beam and a focused ion beam are orthogonally arranged is disclosed (see Japanese Patent Application Laid-open No. Hei 6-231720).

According to the apparatus thus configured, it becomes possible to observe a processed cross-section from a vertical direction without moving the sample stage. It becomes also possible to perform thickness monitoring of a thin film sample for an electron microscope and perform real-time acquisition of a scanning transmission electron microscope image by arranging a transmission electron detector in the incident direction of the electron beam.

In the case of the conventional composite charged particle beam apparatus, the ion beam and the electron beam are used to observe the same plane, for example, the same sample surface, and hence the directions of observation images acquired by the respective beams are coincident with a stage drive direction. On the other hand, in the composite charged particle beam apparatus in which two beams are orthogonally arranged, observation images acquired by the respective beams represent different orthogonal planes, for example, a sample surface and a sample side surface, and hence the vertical and horizontal directions of the respective images are not coincident with the operation directions of the axes of the stage. Therefore, the composite charged particle beam apparatus in which two beams are orthogonally arranged has a problem in that an erroneous operation is apt to occur when an operator adjusts a processing observation position of the sample while looking at the observation image of the focused ion beam or the electron beam.

SUMMARY OF THE INVENTION

The present invention provides a composite charged particle beam apparatus including two charged particle beams orthogonally arranged, which is capable of operating a sample stage of the composite charged particle beam apparatus with, good operability.

In order to achieve the above-mentioned object, the present invention provides the following measures.

According to the present invention, there is provided a composite charged particle beam apparatus, including: a focused ion beam column; an electron beam column, which is arranged substantially at a right angle with respect to the focused ion beam column; a sample stage for moving a sample; a detector for detecting a secondary particle generated from the sample; an observation image formation portion for forming a focused ion beam image and an electron beam image based on a detection signal of the detector; an optical microscope for observing the sample; a display portion capable of displaying the focused ion beam image, the electron beam image, and an optical microscope image; and a stage control portion for moving the sample stage in accordance with a coordinate system of each image displayed on the display portion.

With this configuration, even when a movement direction of the sample stage is specified by coordinate systems of different types of observation images, the single sample stage can be moved in a direction corresponding to each coordinate system.

Further, the display portion of the composite charged particle beam apparatus according to the present invention displays a coordinate system of a drive axis of the sample stage on the optical microscope image.

Further, the stage control portion of the composite charged particle beam apparatus according to the present invention moves the sample stage so that a position specified on one of the focused ion beam image and the electron beam image is displayed at a center of the specified one of the focused ion beam image and the electron beam image.

Further, the stage control portion of the composite charged particle beam apparatus according to the present invention rotates the sample stage about beam irradiation axes of the focused ion beam column and the electron beam column.

According to the composite charged particle beam apparatus of the present invention, which includes two charged particle beams orthogonally arranged, when the operator adjusts a processing observation position of the sample while looking at an observation image of the focused ion beam or the electron beam, the stage can be driven in accordance with the coordinate system of each observation image. Therefore, the position of the sample can be adjusted while preventing a malfunction caused by an erroneous operation.

DETAILED DESCRIPTION OF THE PREFERRED EMBODIMENT

Now, a composite charged particle beam apparatus according to an embodiment of the present invention is described.

Figure 1:
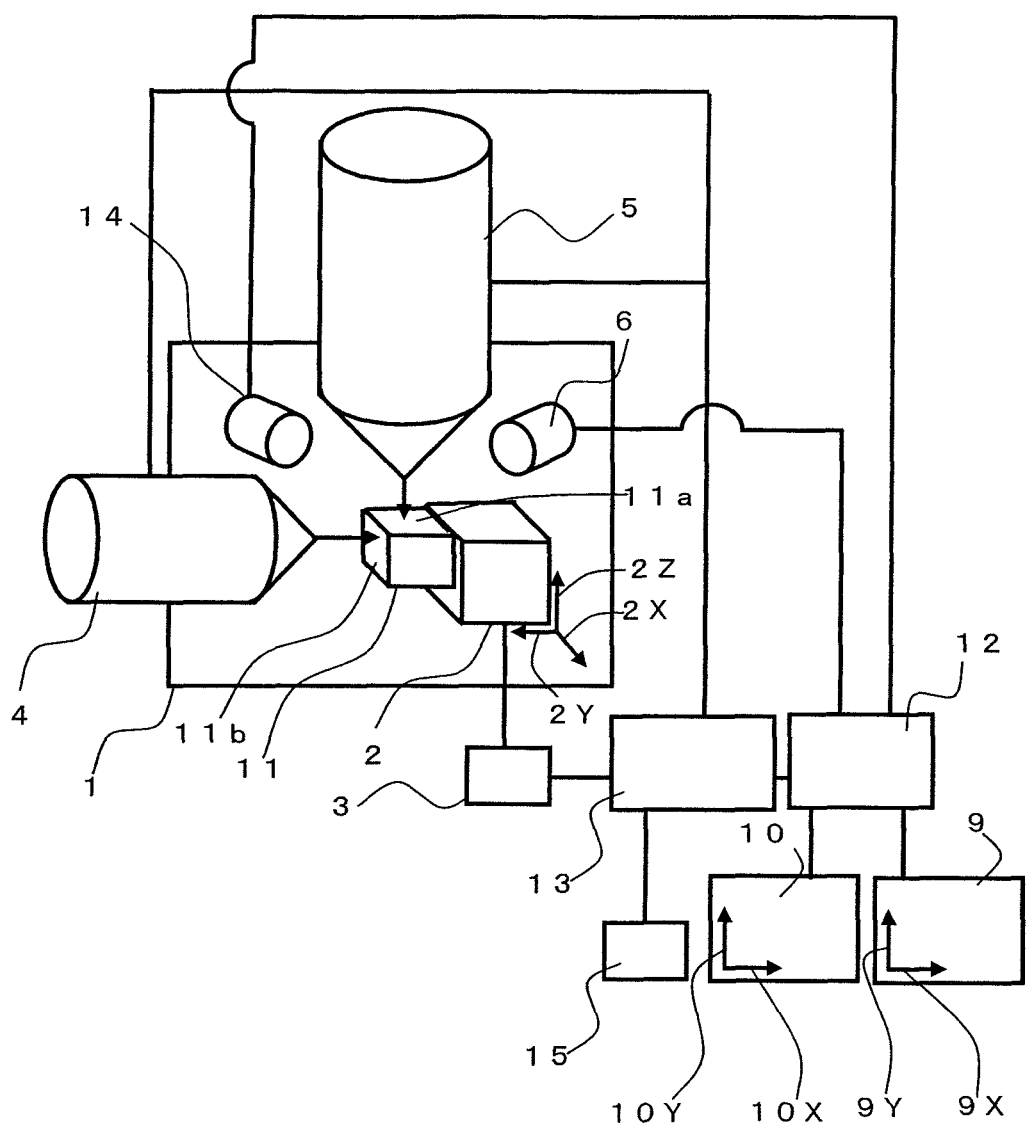
FIG. 1 is a configuration diagram of a composite charged particle beam apparatus according to an embodiment of the present invention.

As illustrated in FIG. 1, the composite charged particle beam apparatus of this embodiment includes a sample stage 2 for moving a sample 11 in a sample chamber 1. The composite charged particle beam apparatus further includes an electron beam column 5 for irradiating the sample 11 with an electron beam and a focused ion beam column 4 for irradiating the sample 11 with a focused ion beam. The electron beam column 5 and the focused ion beam column 4 are arranged so that beam irradiation axes thereof may intersect with each other substantially perpendicularly.

Particles generated from the sample 11 through the irradiation of the focused ion beam or the electron beam are detected by a detector 6, and the acquired particles are subjected to time-series processing by an image formation portion 12, thereby forming an observation image. Note that, the particles generated from the sample 11 include secondary particles, such as electrons, ions, and X-rays, which are generated from the sample 11 through the irradiation of a charged particle beam, and primary particles which are an irradiation beam itself after subjected to scattering and absorption by the sample 11. Specifically, secondary electrons which are generated by irradiating the sample with the electron beam or the ion beam are used to form a focused ion beam image or an electron beam image as a secondary electron image. Reflected electrons which are generated by irradiating the sample with the electron beam are used to form a reflected electron image. Scattered electrons which are generated by irradiating the sample with the electron beam are used to form an EBSD image. X-rays which are generated by irradiating the sample with the electron beam are used to form an EDS image. Further, transmission electrons which are generated by irradiating the sample with the electron beam and have passed through the sample are used to form a transmission electron image.

The formed focused ion beam image is displayed on a first display portion 9, and the formed electron beam image is displayed on a second display portion 10. In this case, the focused ion beam image and the electron beam image may be displayed on a single display portion.

Further, an operator inputs an instruction regarding an apparatus operation via an input portion 15. In response to the input signal, the control portion 13 transmits control signals to a stage control portion 3 for controlling the focused ion beam column 4, the electron beam column 5, and the sample stage 2 and to an image formation portion 12, thereby controlling the composite charged particle beam apparatus.

The stage control portion 3 changes a coordinate system of the sample stage 2 in the movement direction thereof so as to adjust the coordinate system to a coordinate system of an observation system, thereby controlling the movement of the, sample stage 2. Now, how to change the coordinate system of the sample stage 2 in the movement direction is described.

Figure 6:
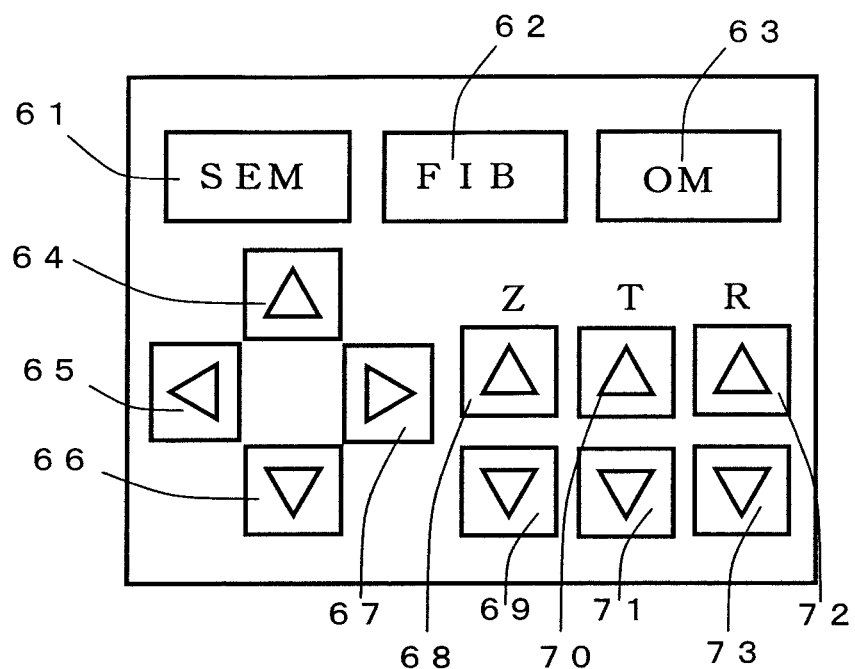
FIG. 6 is a control screen for a sample stage according to the embodiment of the present invention.

FIG. 6 is a control screen for the sample stage 2. The control screen is displayed on a part of the first display portion 9 or the second display portion 10. On the control screen, the operator selects a coordinate system of an observation image to be used for the movement of the sample stage 2. In this case, the focused ion beam image, the electron beam image, and the optical microscope image can be selected by an SEM button 61, an FIB button 62, and an OM button 63, respectively. The stage control portion 3 changes the coordinate system of the sample stage 2 in the movement direction in accordance with the type of a selected observation image.

Then, based on the changed coordinate system of the sample stage 2 in the movement direction, the sample stage 2 is moved with the use of movement buttons 65 and 67 for the X-direction, movement buttons 64 and 66 for the Y-direction, and movement buttons 68 and 69 for the Z-direction. In this way, the sample stage 2 can be moved based on the coordinate system of the selected observation image. Further, the tilt of the sample stage 2 is adjusted by tilt buttons 70 and 71, and the rotation of the sample stage 2 is performed by rotation buttons 72 and 73.

Next, the relationship between an observation image displayed on the display portion and the movement direction of the sample stage 2 is described.

Images are displayed on the first display portion 9 and the second display portion 10 so that the horizontal direction of a plane substantially perpendicular to the beam irradiation direction becomes an X-axis direction, the vertical direction of the plane becomes a Y-axis direction, and the direction parallel to the beam irradiation direction becomes a Z-axis direction.

The X, Y, and Z directions of the focused ion beam image (an X-axis direction 9X, a Y-axis direction 9Y, and a Z-axis direction (not shown) of the focused ion beam image, respectively) correspond to a horizontal direction drive axis (X axis) 2X of the sample stage, a height direction drive axis (Z axis) 2Z of the sample stage, and a vertical direction drive axis (Y axis) 2Y of the sample stage, respectively.

Figure 2:
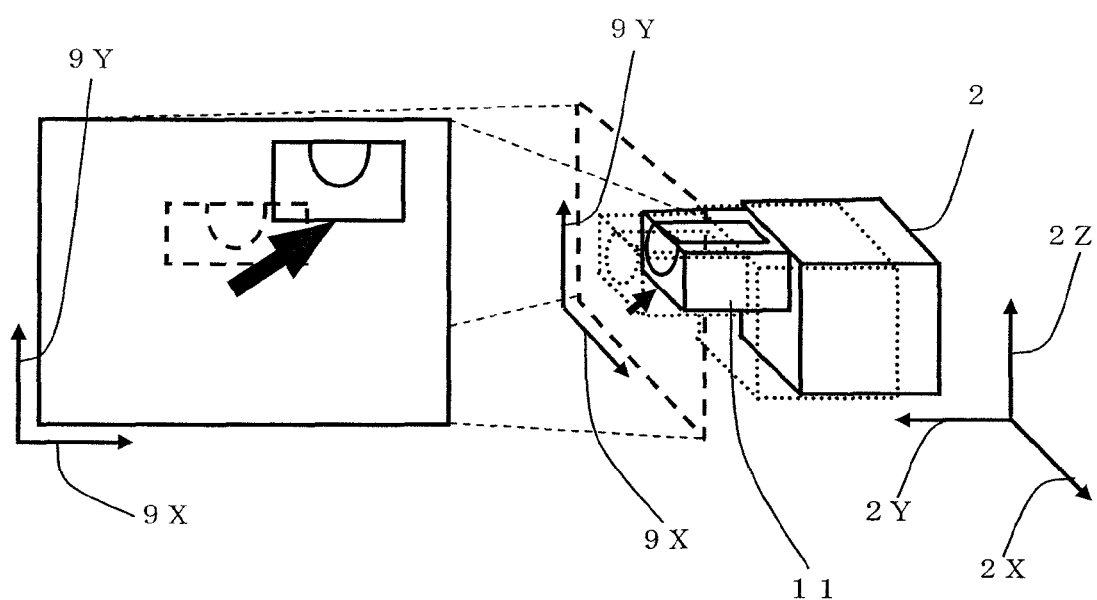
FIG. 2 is a schematic diagram of a stage operation in the case of operating a stage based on a focused ion beam observation image according to the embodiment of the present invention.

As illustrated in FIG. 2, in the case of moving the sample stage 2 in the X-axis direction 9X and the Y-axis direction 9Y of the focused ion beam image on the focused ion beam image illustrated in the left of FIG. 2, the operator inputs an instruction of the movement of the stage in the X-axis direction 9X and the Y-axis direction 9Y of the focused ion beam image to the input portion 15 while looking at the first display portion 9. Then, in response to the instruction, the stage control portion 3 transmits, to the sample stage 2 illustrated in the right of FIG. 2, a drive signal regarding the horizontal direction drive axis (X axis) 2X of the sample stage and the height direction drive axis (Z axis) 2Z of the sample stage, thereby moving the sample stage 2 in the directions of the horizontal direction drive axis (X axis) 2X of the sample stage and the height direction drive axis (Z axis) 2Z of the sample stage. In this way, on the focused ion beam observation image, the sample 11 is moved in the X-axis direction 9X and the Y-axis direction 9Y of the focused ion beam image.

On the other hand, the X, Y, and Z directions of the electron beam image (an X-axis direction 10X, a Y-axis direction 10Y, and a Z-axis direction (not shown) of the electron beam image, respectively) correspond to the horizontal direction drive axis (X axis) 2X of the sample stage, the vertical direction drive axis (Y axis) 2Y of the sample stage, and the height direction drive axis (Z axis) 2Z of the sample stage, respectively.

Figure 3:
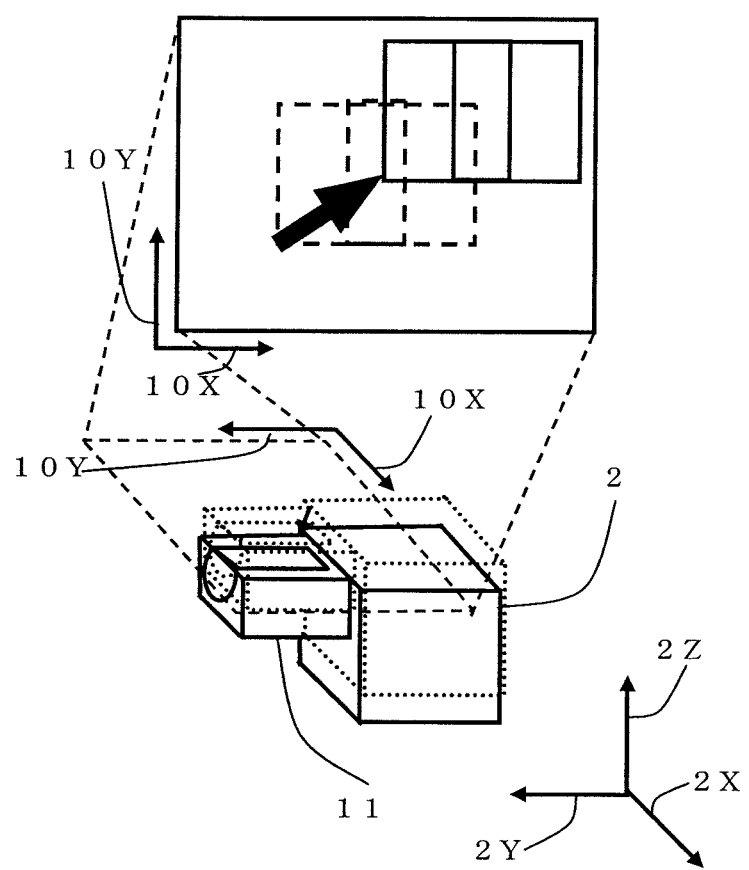
FIG. 3 is a schematic diagram of a stage operation in the case of operating the stage based on an electron beam observation image according to the embodiment of the present invention.

As illustrated in FIG. 3, in the case of moving the sample stage 2 in the X-axis direction 10X and the Y-axis direction 10Y of the electron beam image on the electron beam image illustrated in the top of FIG. 3, the operator inputs an instruction of the movement of the stage in the X-axis direction 10X and the Y-axis direction 10Y of the electron beam image to the input portion 15 while looking at the second display portion 10. Then, in response to the instruction, the stage control portion 3 transmits, to the sample stage 2 illustrated in the bottom of FIG. 3, a drive signal regarding the horizontal direction drive axis (X axis) 2X of the sample stage and the vertical direction drive axis (Y axis) 2Y of the sample stage. In this way, the sample stage 2 is moved in the horizontal direction drive axis (X axis) 2X of the sample stage and the vertical direction drive axis (Y axis) 2Y of the sample stage, and, on the electron beam observation image, the sample 11 is moved in the X-axis direction 10X and the Y-axis direction 10Y of the electron beam image.

The same holds true for an instruction of movement of the sample stage 2 in the Z direction. In the case of instructing the sample stage 2 to move in the Z-axis direction of the focused ion beam image on the focused ion beam image, the vertical direction drive axis (Y axis) 2Y of the sample stage 2 is driven. In the case of instructing the sample stage 2 to move in the Z-axis direction of the electron beam image on the electron beam image, the height direction drive axis (Z axis) 2Z of the sample stage is driven.

The movement of the observation image is not limited to the instruction of the movement direction as described above. Also in the case where a specific position in an observation image is specified and the sample stage 2 is moved so that the specified position may be positioned at the center of the specified observation image, the stage control portion 3 drives the stage axis in accordance with the coordinate system of each observation image.

Figure 4:
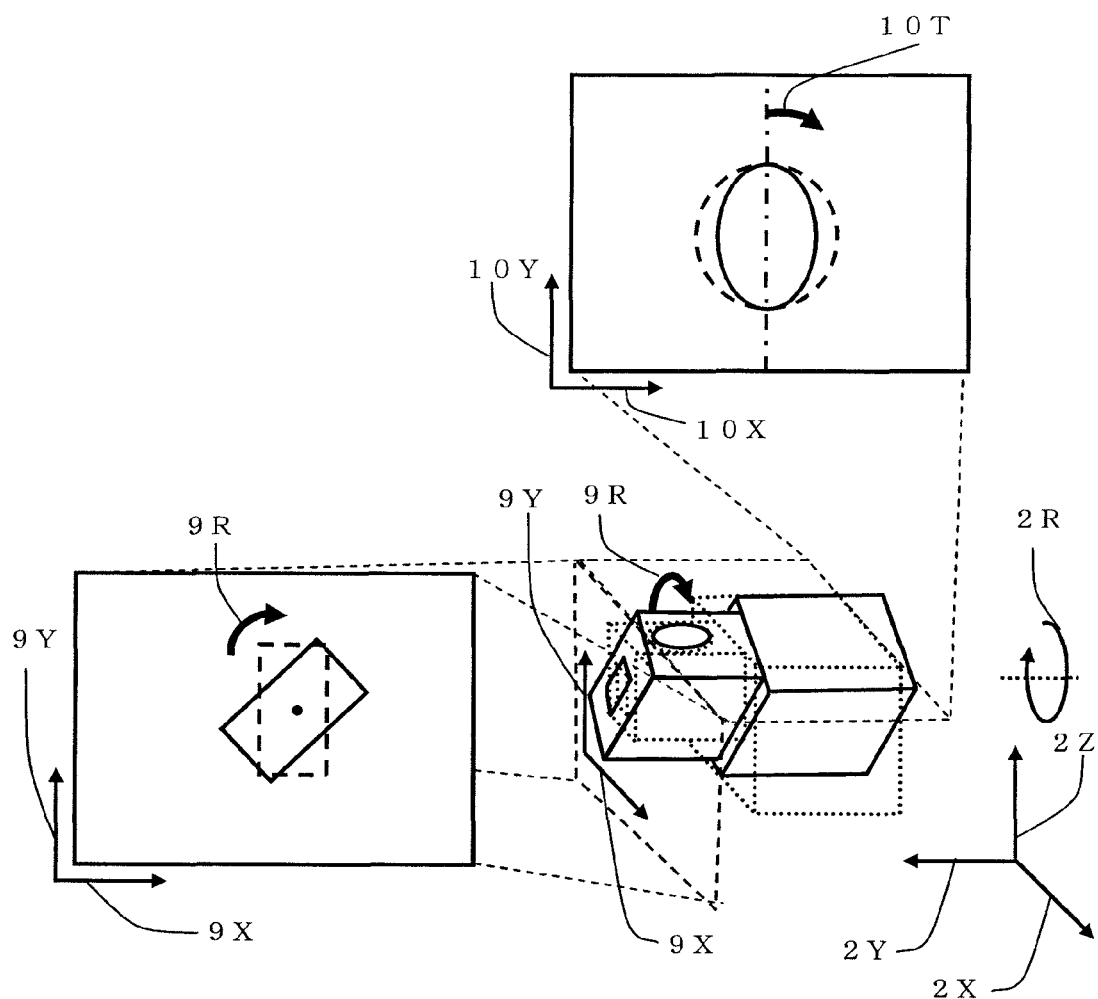
FIG. 4 is a schematic diagram of a stage operation in the case where the stage has a rotation axis substantially parallel to a focused ion beam according to the embodiment of the present invention.

Further, in the case where the sample stage 2 has a rotation axis (R axis) in a direction substantially parallel to one beam irradiation direction, the sample stage 2 performs a rotation operation with respect to one of the beams and the sample stage 2 performs a tilt operation with respect to the other beam. FIG. 4 illustrates the operation of the composite charged particle beam apparatus of this embodiment, which is performed in the case where the sample stage 2 has a rotation drive axis in a direction substantially parallel to the ion beam irradiation direction. In this case, the lower left of FIG. 4 illustrates the focused ion beam image, the upper right thereof illustrates the electron beam image, and the lower right thereof illustrates the sample stage 2.

A rotation direction drive axis 2R of the sample stage, which is parallel to the focused ion beam irradiation direction, is driven in the case where an instruction is issued via the first display portion 9 to move and rotate the sample stage 2 in a clockwise rotation direction 9R about a rotation axis parallel to the focused ion beam. On the other hand, in the second display portion 10, the rotation direction drive axis 2R of the sample stage, which is parallel to the focused ion beam irradiation direction, is driven in the case where an instruction is issued to move and tilt the sample stage 2 in a clockwise rotation direction 10T about a rotation axis substantially perpendicular to the electron beam.

Next, the relationship among the optical microscope image, the sample, and the movement direction of the sample stage 2 is described. The composite charged particle beam apparatus of this embodiment includes an optical microscope 14 so as to enable optical microscope observation of the tips of the focused ion beam column 4 and the electron beam column 5 and the vicinity of the sample stage 2 in the sample chamber 1. The optical microscope 14 is connected to the image formation portion 12, and an optical microscope image is displayed on the first display portion 9 or the second display portion 10.

Figure 5:
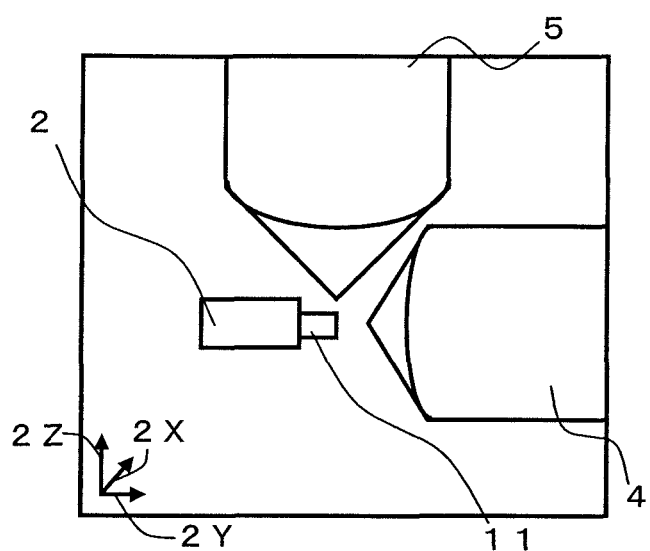
FIG. 5 is an optical microscope image according to the embodiment of the present invention.

FIG. 5 is an optical microscope image observed by the optical microscope 14. The optical microscope image is an observation image whose magnification is lower than those of the focused ion beam image and the electron beam image, and hence the situation in the sample chamber 1 can be easily grasped. In the case where the operator moves the sample stage 2 while looking at the optical microscope image, the stage control portion 3 controls the movement based on a coordinate system of the drive axis of the sample stage 2.

Further, in the optical microscope image, the coordinate system of the drive axis of the sample stage 2 is displayed. With this, the situation in the sample chamber 1 can be observed by the optical microscope image having a low magnification while grasping the drive direction of the sample stage 2. Therefore, the movement operation of the sample stage 2 can be performed safely while preventing the sample 11 from colliding against a tip of the column.

In the above description, an electron beam image is used, but, instead of using the electron beam image, a reflected electron image, a transmission electron image, an EDS image, or an EBSD image can also be used.

What is claimed is:

1. A composite charged particle beam apparatus, comprising:
   a focused ion beam column having an ion beam irradiation axis;
   an electron beam column having an electron beam irradiation axis, the electron beam column being arranged relative to the focused ion beam column so that the beam irradiation axes thereof intersect with each other substantially at a right angle;
   a sample stage movable in accordance with a coordinate system for moving a sample;
   a detector for detecting secondary particles generated from the sample;
   an observation image formation portion for forming a focused ion beam image and an electron beam image based on a detection signal of the detector;
   an optical microscope for observing the sample;
   a display portion capable of displaying the focused ion beam image, the electron beam image, and an optical microscope image on respective coordinate systems; and
   a stage control portion configured to change the coordinate system of the sample stage in the movement direction thereof using a control screen of the display portion to select any one of the coordinate systems of the focused ion beam image, the electron beam image, and the optical microscope image to thereby control movement of the sample stage using movement buttons on a stage control screen of the display portion.

2. A composite charged particle beam apparatus according to claim 1, wherein the display portion displays a coordinate system of a drive axis of the sample stage on the optical microscope image.

3. A composite charged particle beam apparatus according to claim 2, wherein the stage control portion moves the sample stage so that a position specified on one of the focused ion beam image and the electron beam image is displayed at a center of the specified one of the focused ion beam image and the electron beam image.

4. A composite charged particle beam apparatus according to claim 1, wherein the stage control portion rotates the sample stage about beam irradiation axes of the focused ion beam column and the electron beam column.

5. A composite charged particle beam apparatus according to claim 1, wherein the stage control portion moves the sample stage so that a position specified on one of the focused ion beam image and the electron beam image is displayed at a center of the specified one of the focused ion beam image and the electron beam image.

6. A composite charged particle beam apparatus according to claim 5, wherein the stage control portion rotates the sample stage about beam irradiation axes of the focused ion beam column and the electron beam column.

* * * * *